United States Patent [19]
Watt et al.

[11] 4,269,837
[45] May 26, 1981

[54] HYPOGLYCEMIC GUANYLAMIDINES, COMPOSITIONS AND USE

[75] Inventors: David S. Watt, East Lyme, Conn.; Jeffrey L. Ives, King of Prussia, Pa.

[73] Assignee: Pfizer Inc., New York, N.Y.

[21] Appl. No.: 122,155

[22] Filed: Feb. 19, 1980

[51] Int. Cl.³ .................. A61K 31/54; A61K 31/155; C07D 295/12; C07C 129/12
[52] U.S. Cl. .................................. 424/246; 544/363; 544/242; 424/244; 544/295; 544/296; 424/248.51; 544/322; 544/326; 424/248.56; 544/327; 544/328; 424/250; 544/330; 544/331; 424/251; 544/332; 544/333; 424/258; 544/335; 544/360; 424/263; 544/379; 424/267; 544/398; 544/402; 424/274; 546/162; 546/163; 424/275; 546/171; 546/176; 424/285; 546/193; 546/194; 424/326; 546/205; 546/212; 260/239 B; 546/213; 546/214; 260/243.3; 546/231; 546/256; 260/244.4; 546/264; 546/281; 260/326.5 L; 546/283; 546/284; 260/326.5 SM; 546/306; 546/332; 260/326.5 D; 549/60; 549/68; 260/326.84; 549/74; 549/75; 260/326.86; 564/237; 564/238; 260/330.3; 564/239; 260/347.7; 544/122; 544/124; 544/128; 544/146; 544/152; 544/162; 544/165; 544/59; 544/60; 544/62

[58] Field of Search .................... 260/239 B, 326.5 L, 260/326.5 SM, 326.5 D, 326.84, 326.86, 347.7, 243.3, 244.4, 330.3; 564/237, 238, 239; 544/122, 124, 128, 146, 152, 162, 165, 59, 60, 62, 242, 295, 296, 322, 326, 327, 328, 330, 331, 332, 333, 335, 360, 363, 379, 398, 402; 546/162, 163, 171, 193, 194, 205, 212, 213, 214, 231, 256, 264, 281, 283, 284, 306, 332, 176; 549/60, 68, 74, 75; 424/244, 258, 267, 246, 263, 245.51, 274, 248.56, 275, 250, 285, 251, 326

[56] References Cited
FOREIGN PATENT DOCUMENTS
852565 9/1977 Belgium .
478802 11/1969 Switzerland .

OTHER PUBLICATIONS

Birtwell, *J. Chem. Soc.*, (1949), pp. 2561-2566.
Benko et al., *Chem. Abstracts*, vol. 70, (1969), No. 96441p.
Cragoe et al., *Chem. Abstracts*, vol. 71, (1969), No. 305049.

*Primary Examiner*—Henry R. Jiles
*Assistant Examiner*—R. W. Ramsuer
*Attorney, Agent, or Firm*—Francis X. Murphy; Charles J. Knuth; Peter C. Richardson

[57] ABSTRACT

Novel guanylamidines and the pharmaceutically acceptable acid addition salts thereof having activity as hypoglycemic agents are disclosed.

46 Claims, No Drawings

HYPOGLYCEMIC GUANYLAMIDINES, COMPOSITIONS AND USE

BACKGROUND OF THE INVENTION

This invention relates to novel guanylamidines useful for reducing blood sugar levels in warm blooded animals. Accordingly, these compounds are of therapeutic value as hypoglycemic agents in the treatment of diabetes.

Belgian Pat. No. 852,565 discloses a series of N-heteroycyclidine-guanidine derivatives having activity as hypoglycemic agents.

SUMMARY OF THE INVENTION

The present invention relates to novel guanylamidines useful as hypoglycemic agents. More particularly, the compounds of the present invention are those of the formula

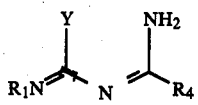
I and the pharmaceutically acceptable acid addition salts thereof, wherein $R_1$ and $R_4$ are each selected from phenyl, phenyl monosubstituted with chloro, bromo, fluoro, alkyl of 1 to 3 carbon atoms or alkoxy of 1 to 3 carbon atoms, benzyl, naphthyl, pyridyl, quinolyl, furyl, thienyl and pyrimidinyl; and Y is

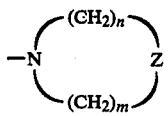

or $-NR_2R_3$,
wherein n and m are each 1, 2 or 3, with the proviso that the sum of n and m is from 3 to 5 and Z is $CH_2$, O, S, SO, $SO_2$, NH or $NCH_3$; and $R_2$ and $R_3$ are each selected from n-alkyl of 1 to 4 carbon atoms, alkoxyethyl, wherein said alkoxy group is of 1 to 3 carbon atoms, phenyl and phenyl monosubstituted with chloro, bromo, fluoro, alkyl of 1 to 3 carbon atoms or alkoxy of 1 to 3 carbon atoms.

Preferably, $R_1$ is phenyl or monosubstituted phenyl, $R_4$ is phenyl, monosubstituted phenyl, benzyl, naphthyl, pyridyl, furyl or thienyl, and Y is pyrrolidinyl, piperidinyl, azacycloheptyl, morpholino, thiomorpholino, piperazinyl, N-methyl-piperazinyl, or $-NR_2R_3$, wherein $R_2$ and $R_3$ are each n-alkyl of 1 to 4 carbon atoms or phenyl.

One group of compounds of interest is that where Y is morpholino, especially where $R_1$ is phenyl or monosubstituted phenyl, including chlorophenyl and methoxyphenol. Of this group, preferred compounds are those where $R_4$ is benzyl, pyridyl, naphthyl, phenyl or monosubstituted phenyl including methoxyphenyl.

Also of interest are compounds wherein Y is thiomorpholino, especially where $R_1$ is phenyl and $R_4$ is phenyl or pyridyl.

Also embraced by the present invention are those compounds where Y is piperazinyl or N-methyl-piperazinyl, preferably such compounds wherein $R_1$ and $R_4$ are each phenyl.

A further group of compounds of interest is that where Y is pyrrolidinyl, especially where $R_1$ is phenyl or monosubstituted phenyl, including chlorophenyl and methoxyphenyl. Preferred compounds are those where $R_4$ is phenyl, monosubstituted phenyl, including chlorophenyl, naphthyl, pyridyl, furyl, thienyl and benzyl.

Also embraced by this invention are compounds where Y is piperadinyl or azacycloheptyl, the preferred compounds for each of these groups being compounds where $R_1$ and $R_4$ are each phenyl.

A further group of compounds of interest is that where Y is $-NR_2R_3$. $R_2$ and $R_3$ are preferably phenyl or n-alkyl of 1 to 4 carbon atoms, especially methyl or ethyl. Preferred compounds are those wherein $R_1$ and $R_4$ are each phenyl.

In addition, compounds having disubstituted phenyl groups as one or more of the $R_1$, $R_2$, $R_3$ and $R_4$ substituents, preferably as the $R_1$ or $R_4$ substituents, in compounds of formula I are also active as hypoglycemic agents. Such substituents include chloro, bromo, fluoro, alkyl of 1 to 3 carbon atoms and alkoxy of 1 to 3 carbon atoms. A preferred disubstituted compound is that where Y is morpholino, $R_1$ is 5-chloro-2-methoxyphenyl and $R_4$ is phenyl.

It will be understood that the compounds of formula I can exist in a number of tautomeric forms, e.g.

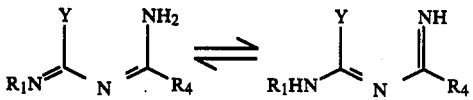

and it is intended that such tautomeric forms are embraced by the specification and claims hereof.

The present invention also embraces pharmaceutical compositions comprising a pharmaceutically acceptable carrier or diluent and an effective blood sugar lowering amount of a compound of formula I. Preferred pharmaceutical compositions of this invention are those containing the preferred compounds of formula I as described hereinabove.

Also embraced by the present invention is a method of lowering blood sugar in the treatment of a diabetic subject which comprises administering to said subject an effective blood sugar lowering amount of a compound of formula I. Preferred compounds for use in this method of treatment are the preferred compounds of formula I, as described hereinabove.

DETAILED DESCRIPTION OF THE INVENTION

The compounds of formula I are readily prepared by the reaction of an appropriate $R_1$, Y-substituted haloamidine, $R_1NC(X)Y$ with an appropriate $R_4$ amidine $R_4C(NH)NH_2$, where $R_1$, Y and $R_4$ are as previously defined and X is halo, preferably chloro. The starting materials are known in the art or are readily prepared by conventional methods known to those skilled in the art.

The $R_1$, Y-substituted haloamidine may be prepared by the reaction of an appropriate $R_1$ isocyanide dihalide $R_1NCX_2$, preferably the dichloride, with an appropriate secondary amine YH, i.e.

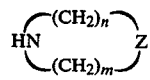

or $R_2R_3NH$,
in accord with the following reaction scheme:

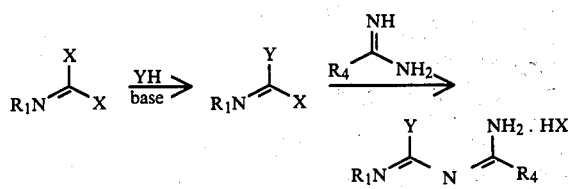

The reaction is generally conducted in an organic solvent, such as diethyl ether, tetrahydrofuran, dioxane, benzene, acetonitrile and the like, at a temperature from about $-25°$ C. to about 35° C., preferably from 0° C. to 25° C. The reaction is conducted in the presence of an organic base such as a tertiary amine, for example a trialkylamine having from 1 to 4 carbon atoms in each alkyl group, preferably triethylamine. Generally, about one equivalent of secondary amine YH and one equivalent of base such as triethylamine per mole of $R_1$ isocyanide dihalide are employed. However, when the secondary amine YH has two nitrogen atoms in the Y radical, i.e. when Z is nitrogen, the reaction is effected without the addition of the base such as triethylamine by employing two equivalents of the amine YH per mole of $R_1$ isocyanide dihalide.

When the secondary amine YH is only weakly basic i.e. the conjugate acid of those compounds having a $pK_a$ less than about 7, for example compounds where Y is $-NR_2R_3$ and one or both of $R_2$ or $R_3$ is phenyl or substituted phenyl, the haloamidine $R_1NC(X)Y$ may be prepared by reaction of the secondary amine YH with an alkyl lithium, for example those having from 1 to 4 carbon atoms in the alkyl group to form the lithium amide Y-Li. A preferred reagent is n-butyl lithium. The reaction is generally conducted in an organic solvent such as hexane, tetrahydrofuran, diethyl ether, dioxane, benzene and the like at a temperature from about $-78°$ C. to about 10° C., preferably from about $-25°$ C. to 0° C. The lithium amide is then reacted with the $R_1$ isocyanide dihalide, as described above, to form the haloamidine $R_1NC(X)Y$. The haloamidine can also be formed by use of an appropriate Grignard reagent in place of an alkyl lithium in order to generate the magnesium amide of the secondary amine YH.

The haloamidine can be isolated from the reaction solution in the procedures described above, if desired, but is preferably not isolated and the solution obtained is used directly in subsequent reaction steps to form the desired product of formula I.

The haloamidine is then reacted with an appropriate $R_4$ amidine $R_4C(NH)NH_2$ to obtain the compound of formula I as the corresponding hydrohalide salt. The reaction is generally conducted in an organic solvent such as diethyl ether, tetrahydrofuran, dioxane, acetonitrile, toluene, benzene, xylene and the like, at a temperature from about $-25°$ C. to about 25° C., preferably $-10°$ C. to 10° C.

A further method of preparing novel compounds of formula I, especially those wherein Y is pyrrolidyl, is by the reaction of an $R_1$ isothiocyanate $R_1NCS$ with an $R_4$ amidine $R_4C(NH)NH_2$, generally in an organic solvent such as an alcohol of 1 to 4 carbon atoms, preferably ethanol or isopropanol, at a temperature from about 0° C. to about 40° C., preferably from 0° C. to 25° C., to form the corresponding $R_1R_4$-substituted thiourea $R_1NHC(S)NC(R_4)NH_2$. The substituted thiourea is then reacted with an alkyl halide having from 1 to 3 carbon atoms, preferably an alkyl iodide and most preferably methyl iodide, in an organic solvent such as an alcohol of 1 to 3 carbon atoms, preferably methanol, generally at reflux temperature to give the corresponding pseudothiourea $R_1NC(SCH_3)NC(R_4)NH_2$ as the hydrohalide salt. The pseudothiourea is then reacted with a secondary amine YH, especially pyrrolidine, to form the desired compound of formula I. The reaction is generally conducted in an organic solvent such as an alcohol of 1 to 4 carbon atoms, such as isopropanol or t-butanol, or in tetrahydrofuran, acetonitrile and the like, at a temperature from about 25° C. to about 75° C., preferably about 25° C. to 50° C. This method of preparation is illustrated by the reaction scheme:

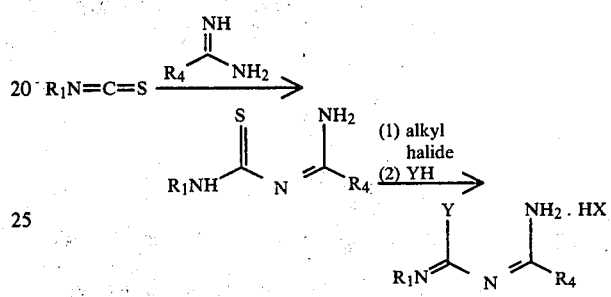

In the methods described above, the desired compound of formula I will be obtained as the hydrohalide salt. The free base can be prepared from the salt by conventional means, for example by contacting with an excess of a base such as an alkali metal hydroxide or carbonate, followed by extraction of the desired free base with a suitable organic solvent, for example dichloromethane, chloroform, diethyl ether and the like.

The pharmaceutically acceptable acid addition salts of the novel compounds of formula I are also embraced by the present invention. The salts are readily prepared by contacting the free base with an appropriate mineral or organic acid in either aqueous solution or in a suitable organic solvent. The solid salt may then be obtained by precipitation or by evaporation of the solvent. The hydrohalide salts may be obtained directly in the methods of preparation described above. The pharmaceutically acceptable acid addition salts of this invention include, but are not limited to, the hydrochloride, hydrobromide, hydroiodide, sulfate, bisulfate, mesylate, nitrate, phosphate, acetate, lactate, maleate, fumarate, citrate, tartrate, succinate, gluconate, and the like. Preferred salts are the hydrochloride, hydroiodide and hydrobromide.

The compounds of formula I and the pharmaceutically acceptable acid addition salts thereof are useful for lowering blood sugar levels in warm blooded animals and accordingly are of therapeutic value as hypoglycemic agents in the treatment of diabetes. The compounds may be administered to a subject in need of treatment by a variety of conventional routes of administration, including orally, parenterally, rectally and sublingually. Preferably, the compounds are administered orally. In general, these compounds will be administered orally at dosages between about 0.5 and 50 mg/kg body weight of the subject to be treated per day, preferably from about 2 to 25 mg/kg per day. However, some variation in dosage will necessarily occur depending on the condition of the subject being treated and the particular compound employed and the person responsible for administration will, in any event, determine the appropriate dose for the individual subject.

The compounds may be administered alone or in combination with pharmaceutically acceptable carriers, in either single or multiple doses. Suitable pharmaceutical carriers include inert diluents or fillers, sterile aqueous solutions and various organic solvents. The pharmaceutical compositions formed by combining the novel compounds of formula I or salts thereof and pharmaceutically acceptable carriers are then readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients such as sodium citrate, calcium carbonate, calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matters or dyes, and if desired, emulsifying agents or suspending agents, together with diluents such as water, ethanol, propylene glycol, glycerin and combinations thereof.

Preferably, the compound is administered orally in unit dosage form, i.e. as a single physically discrete dosage unit containing an appropriate amount of the active compound in combination with a pharmaceutically acceptable carrier or diluent. Examples of such unit dosage forms are tablets or capsules containing from about 50 to 1000 mg of the active ingredient, the compound of formula I comprising from about 10% to 90% of the total weight of the dosage unit.

The ability of the present compounds to decrease blood sugar levels is readily demonstrated by standard pharmacological tests well known to those skilled in the art. For example, the lowering of blood glucose levels in rats may be determined by administering a test compound to rats at a suitable dose, injecting the rat with a glucose solution and determining blood glucose levels at intervals of time thereafter.

The present invention is illustrated by the following examples. However, it should be understood that the invention is not limited to the specific details of these examples.

EXAMPLE 1

N-(1-Amino-1-phenylmethylene)-N'-phenyl-4-morpholinecarboximidamide hydrochloride To 3.48 g (0.02 mol) of phenylisocyanide dichloride in 25 ml of anhydrous ether at 0° C. under a nitrogen atmosphere was added 1.74 g (0.02 mol) of morpholine and 2.02 g (0.02 mol) of triethylamine in 20 ml of ether dropwise. The mixture was stirred for 22 hours and filtered to remove the precipitated triethylamine hydrochloride. To a solution of 4.8 g (0.04 mol) of benzamidine in 15 ml of anhydrous tetrahydrofuran at 0° C. was added the above filtrate dropwise. The mixture was stirred for 22 hours at ambient temperature. The precipitated crude product was collected, washed with anhydrous ether, chromatographed on 150 g of silica gel using 1:6 methanol-dichloromethane and recrystallized from methanol-ether to afford 2.26 g (32%) of N-(1-amino-1-phenylmethylene)-N'-phenyl-4-morpholinecarboximidamide hydrochloride, mp 247°–248° C.

Analysis: Calcd: C, 62.69; H, 6.14; N, 16.25. Found: C, 62.37; H, 6.25; N, 16.16.

EXAMPLE 2

N-(1-Amino-1-phenylmethylene)-N'-(phenyl)-1-methyl-4-piperazinecarboximidamide hydrochloride To 3.48 g (0.02 mol) of phenylisocyanide dichloride in 25 ml of anhydrous ether at 0° C. under a nitrogen atmosphere was added 4.0 g (0.04 mol) of 1-methylpiperazine in 20 ml of anhydrous ether dropwise. The mixture was stirred for one hour at ambient temperature and filtered to remove the precipitated 1-methylpiperazine hydrochloride. The filtrate was added dropwise to a solution of 4.8 g (0.04 mol) of benzamidine in 15 ml of tetrahydrofuran. The mixture was stirred for 20 hours at ambient temperature. The precipitated product was collected and reprecipitated twice by pouring a methanolic solution of the product into a large excess of anhydrous ether. The product was subsequently recrystallized from methanol-ether to afford 2.30 g (32%) of N-(1-amino-1-phenylmethylene)-N'-(phenyl)-1-methyl-4-piperazinecarboximidamide hydrochloride, mp 247°–248° C.

Analysis: Calcd: C, 63.76; H, 6.76; N, 19.57. Found: C, 63.50; H, 6.89; N, 19.60.

EXAMPLE 3

(N-Methyl-N,N'-diphenylguanyl)benzimidamide hydrochloride

To 2.14 g (0.02 mol) of N-methylaniline in 20 ml of anhydrous tetrahydrofuran at 0° C. under a nitrogen atmosphere was added 8 ml of 2.5 M n-butyl lithium in hexane. The solution was stirred for one hour at 0° C. To the lithium N-methylanilide solution at −23° C. was added 3.48 g (0.02 mol) of phenyl isocyanide dichloride in 5 ml of tetrahydrofuran dropwise. The mixture was stirred for 15 minutes at −23° C. and one hour at 0° C. to afford a clear yellow solution to which 4.8 g (0.04 mol) of benzamidine in 15 ml of tetrahydrofuran was added dropwise. The mixture was stirred for 21 hours at ambient temperature, concentrated and chromatographed on 150 g of silica gel using 1:6 methanol-dichloromethane. The chromatographed product was precipitated by adding a methanolic solution of the product to a large volume of ether and finally recrystallized twice from methanol-ether to afford 1.72 g (24%) of (N-methyl-N,N'-diphenylguanyl)benzimidamide hydrochloride, mp 243°–244° C.

Analysis: Calcd: C, 69.32; H, 5.54; N, 15.40. Found: C, 69.16; H, 5.89; N, 15.28.

EXAMPLE 4

N-(1-Amino-1-phenylmethylene)-N'-(phenyl)-1-pyrrolidinecarboximidamide hydroiodide A stirred solution of 6.08 g (0.045 mol) of phenylisothiocyanate and 4.80 g (0.04 mol) of benzamidine in isopropanol was stirred for 18 hours, concentrated and the residue was crystallized from hexane to give 8.0 g (80%) of N-benzimidioyl-N'-phenylthiourea, mp 118°–119° C. A stirred solution of 7.0 g (0.027 mol) of this thiourea and 61.0 g (0.43 mol) of methyl iodide in 200 ml of methanol was refluxed for 18 hours, concentrated, and the residue was crystallized from acetone/ether to give 6.6 g (61%) of the corresponding pseudothiourea, mp 163°–165° C. A stirred solution of 3.81 g (10 mmol) of this pseudothiourea and 2.13 g (30 mmol) of pyrrolidine in 100 ml of tert-butanol was heated at 70° C. under nitrogen atmosphere for 24 hours. The resulting suspension was filtered and recrystallized from ethanol to give 2.05 g (50%) of N-(1-amino-1-phenylmethylene)-N'-(phenyl)-1-pyrrolidinecarboximidamide hydroiodide, mp 243°–244° C.

Analysis: Calcd: C, 51.44; H, 5.04; N, 13.33. Found: C, 51.53; H, 5.33; N, 13.07.

EXAMPLES 5–29

The following compounds were prepared by the procedure of Example 1 using the appropriately substituted starting materials.

EXAMPLE 5

N-(1-amino-1-(2-pyridyl)methylene)-N'-phenyl-4-morpholinecarboximidamide hydrochloride, 23% yield, mp 229°–230° C. (d).

Analysis: Calcd: C, 59.04; H, 5.83; N, 20.25. Found: C, 59.15; H, 6.08; N, 20.27.

EXAMPLE 6

N-(1-amino-1-(3-pyridyl)methylene)-N'-phenyl-4-morpholinecarboximidamide hydrochloride, 6% yield, mp 212°–214° C. (d).

Exact Mass (free base): Calcd: 309.1589; Found: 309.1615.

EXAMPLE 7

N-(1-amino-1-(2-methoxyphenyl)methylene)-N'-phenyl-4-morpholinecarboximidamide hydrochloride, 14% yield, mp 224.5°–226° C.

Analysis: Calcd: C, 60.87; H, 6.18; N, 14.95. Found: C, 60.58; H, 6.31; N, 14.87.

EXAMPLE 8

N-(1-amino-2-phenylethylidene)-N'-phenyl-4-morpholinecarboximidamide hydrochloride, 15% yield, mp 232°–233.5° C. (d).

Analysis: Calcd: C, 63.59; H, 6.46; N, 15.61. Found: C, 63.20; H, 6.42; N, 15.59.

EXAMPLE 9

N-(1-amino-1-(1-naphthyl)methylene-N'-phenyl-4-morpholinecarboximidamide hydrochloride, 11% yield, mp 233.5°–234.5° C.

Exact Mass (free base): Calcd: 358.1793; Found: 358.1814.

EXAMPLE 10

N-(1-amino-1-phenylmethylene)-N'-(4-methoxyphenyl)-4-morpholinecarboximidamide hydrochloride ¼ hydrate, 29% yield, mp 234.5°–235.5° C.

Analysis: Calcd: C, 60.15; H, 6.24; N, 14.77. Found: C, 59.95; H, 6.07; N, 14.74.

Exact Mass (free base): Calcd: 338.1743; Found: 338.1720.

EXAMPLE 11

N-(1-amino-1-phenylmethylene)-N'-(4-chlorophenyl)-4-morpholinecarboximidamide hydrochloride, 33% yield, mp 246°–247° C.

Analysis: Calcd: C, 57.00; H, 5.32; N, 14.77. Found: C, 57.13; H, 5.50; N, 14.65.

EXAMPLE 12

N-(1-amino-1-phenylmethylene)-N'-(3-chlorophenyl)-4-morpholinecarboximidamide hydrochloride, 6% yield, mp 241°–242° C.

Analysis: Calcd: C, 57.00; H, 5.32; N, 14.77. Found: C, 56.68; H, 5.16; N, 14.69.

EXAMPLE 13

N-(1-amino-1-phenylmethylene)-N'-(5-chloro-2-methoxyphenyl)-4-morpholinecarboximidamide hydrochloride, 2% yield, mp 239.5°–240.5° C.

Exact Mass (free base): Calcd: 372.1353, 374.1323; Found: 372.1332, 374.1318.

EXAMPLE 14

N-(1-amino-1-phenylmethylene)-N'-phenyl-4-thiomorpholinecarboximidamide hydrochloride, 51% yield, mp 265°–266° C.

Analysis: Calcd: C, 59.90; H, 5.87; N, 15.52. Found: C, 59.87; H, 5.81; N, 15.68.

EXAMPLE 15

N-(1-amino-1-(2-pyridyl)methylene)-N'-phenyl-4-thiomorpholinecarboximidamide hydrochloride, 6% yield, mp 230°–232° C. (d).

Exact Mass: Calcd: 325.1361; Found: 325.1355.

EXAMPLE 16

N-(1-amino-1-phenylmethylene)-N'-phenyl-1-pyrrolidinecarboximidamide hydrochloride, 37% yield, mp 274°–275° C.

Analysis: Calcd: C, 65.74; H, 6.44; N, 17.04; Found: C, 65.50; H, 6.21; N, 16.65.

EXAMPLE 17

N-(1-amino-1-(4-chlorophenyl)methylene)-N'-phenyl-1-pyrrolidinecarboximidamide hydrochloride, 48% yield, mp 293°–295° C.

Exact Mass (free base): Calcd: 326.1299, 328.1268; Found: 326.1270, 328.1240.

EXAMPLE 18

N-(1-amino-1-(1-naphthyl)methylene)-N'-phenyl-1-pyrrolidinecarboximidamide hydrochloride ⅛ hydrate, 46% yield, mp 258°–260° C.

Analysis: Calcd: C, 69.32; H, 6.15; N, 14.70. Found: C, 69.15; H, 6.11; N, 14.74.

EXAMPLE 19

N-(1-amino-1-(2-pyridyl)methylene)-N'-phenyl-1-pyrrolidinecarboximidamide, 11% yield, mp 167°–169° C.

Analysis: Calcd: C, 69.60; H, 6.53; N, 23.88. Found: C, 69.34; H, 6.49; N, 23.97.

EXAMPLE 20

N-(1-amino-1-(3-pyridyl)methylene-N'-phenyl-1-pyrrolidinecarboximidamide hydrochloride ¼ hydrate, 11% yield, mp 274°–275° C.

Analysis: Calcd: C, 61.07; H, 6.18; N, 20.95. Found: C, 61.01; H, 6.21; N, 21.14.

EXAMPLE 21

N-(1-amino-1-(4-pyridyl)methylene)-N'-phenyl-1-pyrrolidinecarboximidamide hydrochloride, 13% yield, mp 268°–270° C.

Exact Mass (free base): Calcd: 293.1640. Found: 293.1619.

EXAMPLE 22

N-(1-amino-1-(2-furyl)methylene)-N'-phenyl-1-pyrrolidinecarboximidamide hydrochloride, 69% yield, mp 258°–259° C.

Analysis: Calcd: C, 60.28; H, 6.01; N, 17.58. Found: C, 59.86; H, 6.05; N, 17.65.

Exact Mass (free base): Calcd: 282.1481. Found: 282.1460.

EXAMPLE 23

N-(1-amino-1-(2-thienyl)methylene)-N'-phenyl-1-pyrrolidinecarboximidamide hydrochloride, 62% yield, mp 269°–273° C. (d).

Analysis: Calcd: C, 57.38; H, 5.72; N, 16.73. Found: C, 57.49; H, 5.86; N, 16.56.

EXAMPLE 24

N-(1-amino-1-phenylmethylene)-N'-(4-methoxyphenyl)-1-pyrrolidinecarboximidamide hydrochloride, 40% yield, mp 237°–238° C.

Exact Mass (free base): Calcd: 322.1793. Found: 322.1747.

EXAMPLE 25

N-(1-amino-1-phenylmethylene)-N'-(4-chlorophenyl)-1-pyrrolidinecarboximidamide hydrochloride, 19% yield, mp 220°–223° C.

Exact Mass (free base): Calcd: 326.1299, 328.1268. Found: 326.1267, 328.1319.

EXAMPLE 26

N-(1-amino-2-phenylethylidene)-N'-phenyl-1-pyrrolidinecarboximidamide hydrochloride ¼ hydrate, 22% yield, mp 221°–222° C.

Analysis: Calcd: C, 65.69; H, 6.82; N, 16.13. Found: C, 65.53; H, 6.92; N, 15.83.

EXAMPLE 27

N-(1-amino-1-phenylmethylene)-N'-phenyl-1-piperidinecarboximidamide hydrochloride, 42% yield, mp 248°–250° C.

Analysis: Calcd: C, 66.56; H, 6.76; N, 16.34. Found: C, 66.38; H, 6.71; N, 16.32.

EXAMPLE 28

N-(1-amino-1-phenylmethylene)-N'-phenyl-1-azacycloheptane-1-carboximidamide hydrochloride, 15% yield, mp 249°–250° C.

Analysis: Calcd: C, 67.30; H, 7.06; N, 15.70. Found: C, 67.19; H, 6.68; N, 15.74.

EXAMPLE 29

(N,N-diethyl-N'-phenylguanyl)benzimidamide hydrochloride, 16% yield, mp 227°–228° C.

Analysis: Calcd: C, 65.34; H, 7.01; N, 16.94. Found: C, 65.13; H, 6.95; N, 16.94.

EXAMPLE 30

Following the procedure of Example 3, (N,N,N'-triphenylguanyl)benzimidamide hydrochloride was prepared in 15% yield, mp 214°–215° C.

Analysis: Calcd: C, 73.14; H, 5.43; N, 13.12. Found: C, 72.72; H, 5.49; N, 12.97.

EXAMPLE 31

The procedure of Example 1 may be repeated using the appropriately substituted starting materials to form the hydrohalide salts of the compounds of formula I wherein (1) Y is thiomorpholino; $R_1$ is phenyl, 2-pyridyl, 2-furyl or 2-thienyl; and where, for each value of $R_1$, $R_4$ is 2-methoxyphenyl, 2-chloro-6-methoxyphenyl, 2-fluoro-6-methoxyphenyl, 2,6-dimethoxyphenyl, 5-chloro-2-methoxyphenyl or 5-fluoro-2-methoxyphenyl; (2) Y is thiomorpholino-S-oxide; $R_1$ is phenyl; and $R_4$ is 2-methoxyphenyl, 2-chloro-6-methoxyphenyl, 2-fluoro-6-methoxyphenyl, 2,6-dimethoxyphenyl, 5-chloro-2-methoxyphenyl or 5-fluoro-2-methoxyphenyl; or (3) Y is morpholino; $R_1$ is phenyl, 2-pyridyl, 2-furyl or 2-thienyl; and where, for each value of $R_1$, $R_4$ is 2-methoxyphenyl, 2-chloro-6-methoxyphenyl, 2-fluoro-6-methoxyphenyl, 2,6-dimethoxyphenyl, 5-chloro-2-methoxyphenyl, 5-fluoro-2-methoxyphenyl, 2-ethoxyphenyl or 2-furyl.

EXAMPLE 32

The ability of compounds of the present invention to lower blood glucose levels was demonstrated by the following procedure: 18–24 hour fasted male Sprague-Dawley rats, (180–220 gms) were weighed, numbered and recorded in groups of five as needed. The groups were then dosed with the test compound at a dose of 25 or 50 mg/kg p.o. One hour later the animals were bled from the tail vein and then dosed with glucose (1 gm/kg i.p.). Blood glucose was determined by taking samples from the tail vein at intervals of time. The samples were diluted 1:10 in 0.1% heparinized saline and glucose determinations were made on an Auto-Analyzer.

Results obtained for the compounds of Examples 1 to 30, statistically significant at the 95% confidence level, are shown in Table 1.

TABLE 1

| Example No. | Dose mg/kg | % Decrease in Blood Glucose At | | | |
|---|---|---|---|---|---|
| | | ½ hr | 1 hr | 2 hr | 3 hr |
| 1 | 25 | 21 | 28 | | |
| 2 | 50 | | | 29 | |
| 3 | 50 | 16 | 14 | 24 | |
| 4 | 50 | 16 | 12 | 10 | |
| 5 | 50 | 30 | 35 | | |
| 6 | 25 | | | | 13 |
| 7 | 25 | 30 | | | 24 |
| 8 | 25 | 20 | 24 | | |
| 9 | 25 | | | | 23 |
| 10 | 50 | | 24 | 23 | 19 |
| 11 | 50 | | 15 | 26 | |
| 12 | 25 | | 14 | 21 | |
| 13 | 25 | | | 17 | 19 |
| 14 | 50 | 17 | | 26 | |
| 15 | 25 | | 19 | 21 | 14 |
| 16 | 50 | | | 22 | |
| 17 | 50 | | 10 | 20 | 18 |
| 18 | 50 | 19 | 18 | | |
| 19 | 50 | 30 | | 30 | |
| 20 | 50 | | 18 | | |
| 21 | 50 | | 10 | 13 | |
| 22 | 50 | 25 | 14 | | |
| 23 | 50 | | | | 9 |
| 24 | 50 | | | 15 | 22 |

TABLE 1-continued

| Example No. | Dose mg/kg | % Decrease in Blood Glucose At | | |
|---|---|---|---|---|
| | | ½ hr | 1 hr | 2 hr | 3 hr |
| 25 | 50 | | | 10 | 16 |
| 26 | 25 | 10 | | | 11 |
| 27 | 50 | | 19 | 33 | |
| 28 | 50 | 16 | 25 | | |
| 29 | 25 | | 32 | | |
| 30 | 50 | | 10 | 20 | 15 |

We claim:

1. A compound of the formula

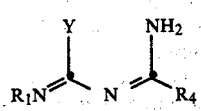

and the pharmaceutically acceptable acid addition salts thereof, wherein $R_1$ and $R_4$ are each selected from phenyl; phenyl monosubstituted with chloro, bromo, fluoro, alkyl of 1 to 3 carbon atoms or alkoxy of 1 to 3 carbon atoms; benzyl; naphthyl, pyridyl, quinolyl; furyl, thienyl and pyrimidinyl;

and Y is

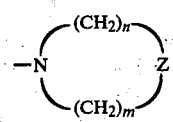

or $-NR_2R_3$, wherein n and m are each 1, 2 or 3, with the proviso that the sum of n and m is from 3 to 5;

Z is $CH_2$, O, S, SO, $SO_2$, NH or $NCH_3$;

and $R_2$ and $R_3$ are each selected from n-alkyl of 1 to 4 carbon atoms; alkoxyethyl, wherein said alkoxy group is of 1 to 3 carbon atoms; phenyl; and phenyl monosubstituted with chloro, bromo, fluoro, alkyl of 1 to 3 carbon atoms or alkoxy of 1 to 3 carbon atoms.

2. A compound of claim 1 wherein $R_1$ is phenyl or monosubstituted phenyl;

$R_4$ is phenyl, monosubstituted phenyl, benzyl, naphthyl, pyridyl, furyl, or thienyl;

and Y is pyrrolidinyl, piperidinyl, azacycloheptyl, morpholino, thiomorpholino, piperazinyl, N-methyl-piperazinyl, or $-NR_2R_3$, wherein $R_2$ and $R_3$ are each n-alkyl of 1 to 4 carbon atoms or phenyl.

3. A compound of claim 1 wherein Y is morpholino.
4. A compound of claim 3 wherein $R_1$ is phenyl.
5. A compound of claim 4 wherein $R_4$ is phenyl.
6. A compound of claim 4 wherein $R_4$ is o-methoxyphenyl.
7. A compound of claim 4 wherein $R_4$ pyridyl.
8. A compound of claim 4 wherein $R_4$ is naphthyl.
9. A compound of claim 4 wherein $R_4$ is benzyl.
10. A compound of claim 3 wherein $R_1$ is p-methoxyphenyl and $R_4$ is phenyl.
11. A compound of claim 3 wherein $R_1$ is p-chlorophenyl and $R_4$ is phenyl.
12. A compound of claim 3 wherein $R_1$ is m-chlorophenyl and $R_4$ is phenyl.
13. N-(1-amino-1-phenylmethylene)-N'-(5-chloro-2-methoxyphenyl)-4-morpholinecarboximidamide.
14. A compound of claim 1 wherein Y is thiomorpholino.
15. A compound of claim 14 wherein $R_1$ is phenyl.
16. A compound of claim 15 wherein $R_4$ is phenyl.
17. A compound of claim 15 wherein $R_4$ is pyridyl.
18. A compound of claim 1 wherein Y is piperazinyl or N-methyl-piperazinyl.
19. A compound of claim 18 wherein $R_1$ and $R_4$ are each phenyl.
20. A compound of claim 1 wherein Y is pyrrolidinyl.
21. A compound of claim 20 wherein $R_1$ is phenyl.
22. A compound of claim 21 wherein $R_4$ is phenyl.
23. A compound of claim 21 wherein $R_4$ is p-chlorophenyl.
24. A compound of claim 21 wherein $R_4$ is naphthyl.
25. A compound of claim 21 wherein $R_4$ is pyridyl.
26. A compound of claim 21 wherein $R_4$ is furyl.
27. A compound of claim 21 wherein $R_4$ is thienyl.
28. A compound of claim 21 wherein $R_4$ is benzyl.
29. A compound of claim 20 wherein $R_1$ is p-methoxyphenyl and $R_4$ is phenyl.
30. A compound of claim 20 wherein $R_1$ is p-chlorophenyl and $R_4$ is phenyl.
31. A compound of claim 1 wherein Y is piperidinyl.
32. A compound of claim 31 wherein $R_1$ and $R_4$ are each phenyl.
33. A compound of claim 1 wherein Y is azacycloheptyl.
34. A compound of claim 33 wherein $R_1$ and $R_4$ are each phenyl.
35. A compound of claim 1 wherein Y is $-NR_2R_3$ and $R_2$ and $R_3$ are each selected from n-alkyl of 1 to 4 carbon atoms and phenyl.
36. A compound of claim 35 wherein $R_1$ and $R_4$ are each phenyl.
37. A compound of claim 36 wherein $R_2$ and $R_3$ are each phenyl.
38. A compound of claim 36 wherein $R_2$ is phenyl and $R_3$ is methyl.
39. A compound of claim 36 wherein $R_2$ and $R_3$ are each n-alkyl of 1 to 4 carbon atoms.
40. A compound of claim 39 wherein $R_2$ and $R_3$ are each ethyl.
41. A pharmaceutical composition comprising a pharmaceutically acceptable carrier and an effective blood-sugar lowering amount of a compound of claim 1.
42. A composition of claim 41 wherein Y is morpholino and $R_1$ and $R_4$ are each phenyl.
43. A composition of claim 41 wherein Y is thiomorpholino and $R_1$ and $R_4$ are each phenyl.
44. A method for lowering blood-sugar in the treatment of a diabetic subject which comprises administering to said subject an effective blood-sugar lowering amount of a compound of claim 1.
45. A method of claim 44 wherein Y is morpholino and $R_1$ and $R_4$ are each phenyl.
46. A method of claim 44 wherein Y is thiomorpholino and $R_1$ and $R_4$ are each phenyl.

* * * * *